United States Patent
Faber et al.

(10) Patent No.: US 7,570,990 B2
(45) Date of Patent: Aug. 4, 2009

(54) DETECTOR FOR ATRIAL FIBRILLATION AND FLUTTER

(75) Inventors: Thomas S. Faber, Freiburg (DE); Michael Lippert, Ansbach (DE); Marc Oliver Schweika-Kresimon, Herne (DE)

(73) Assignee: Biotronik CRM Patent AG, Baar (CH)

(*) Notice: Subject to any disclaimer, the term of this patent is extended or adjusted under 35 U.S.C. 154(b) by 369 days.

(21) Appl. No.: 11/541,054

(22) Filed: Sep. 29, 2006

(65) Prior Publication Data

US 2007/0078356 A1    Apr. 5, 2007

(30) Foreign Application Priority Data

Sep. 30, 2005   (DE) .................... 10 2005 047 320

(51) Int. Cl.
*A61B 5/04* (2006.01)
(52) U.S. Cl. .............. 600/518; 600/509; 600/515; 607/14
(58) Field of Classification Search ........... 600/515, 600/518; 607/4–5, 7–8, 27–28
See application file for complete search history.

(56) References Cited

U.S. PATENT DOCUMENTS

| | | | |
|---|---|---|---|
| 4,291,699 | A | 9/1981 | Geddes et al. |
| 5,058,583 | A | 10/1991 | Geddes et al. |
| 5,267,559 | A | 12/1993 | Jin et al. |
| 5,433,729 | A | 7/1995 | Adams et al. |
| 5,464,431 | A | 11/1995 | Adams et al. |
| 5,464,432 | A | 11/1995 | Infinger et al. |
| 5,486,199 | A | 1/1996 | Kim et al. |
| 5,720,295 | A | 2/1998 | Greenhut et al. |
| 2004/0010201 | A1* | 1/2004 | Korzinov et al. ........... 600/518 |
| 2004/0078058 | A1* | 4/2004 | Holmstrom et al. ........... 607/17 |
| 2004/0249420 | A1* | 12/2004 | Olson et al. .................... 607/9 |

(Continued)

FOREIGN PATENT DOCUMENTS

DE   199 28 659    12/2000

(Continued)

OTHER PUBLICATIONS

German Search Report, dated Jun. 6, 2006.

(Continued)

*Primary Examiner*—Carl H Layno
*Assistant Examiner*—Jennifer Stewart
(74) *Attorney, Agent, or Firm*—Dalina Law Group, P.C.

(57) ABSTRACT

Atrial fibrillation or flutter detector having impedance unit, with measurement input, connected to atrial electrode line having electrode for unipolar measurement of atrium impedance and implemented to generate atrial impedance signal obtained in unipolar manner so that impedance signal comprises multiple impedance values detected at different instants within particular atrial cycle for each atrial cycle, comprising atrial contraction and the following relaxation of the atrium, and having a signal input, via which ventricle signal is supplied to detector, which reflects instants of ventricular contractions in chronological assignment to impedance signal, the detector having an analysis unit, implemented to average multiple sequential impedance signal sections of unipolar atrial impedance signal, delimited by two sequential ventricular contractions with one another and determine maximum amplitude of averaged unipolar atrial impedance signal section, compare to comparison value, and if maximum amplitude of averaged unipolar atrial impedance signal<comparison value, generate AF suspicion signal.

14 Claims, 4 Drawing Sheets

U.S. PATENT DOCUMENTS

| | | | |
|---|---|---|---|
| 2005/0080347 A1* | 4/2005 | Sheth et al. | 600/515 |
| 2005/0159667 A1* | 7/2005 | Korzinov | 600/516 |
| 2006/0142811 A1* | 6/2006 | Militello | 607/9 |
| 2007/0055170 A1* | 3/2007 | Lippert et al. | 600/547 |

FOREIGN PATENT DOCUMENTS

| | | |
|---|---|---|
| DE | 10 2004 034 337 | 3/2005 |
| DE | 103 61 143 | 3/2005 |
| EP | 05 83 499 | 8/1992 |
| EP | 1384433 | 1/2004 |
| WO | WO 2004/028629 | 4/2004 |

OTHER PUBLICATIONS

European Search Report, dated Jun. 10, 2008.

\* cited by examiner

DETECTOR FOR ATRIAL FIBRILLATION AND FLUTTER

This application takes priority from German Patent Application DE 10 2005 047 320.2 filed Sep. 30, 2005 the specification of which is hereby incorporated herein by reference.

BACKGROUND OF THE INVENTION

1. Field of the Invention

The present invention relates to a detector for atrial fibrillation and atrial flutter ("AF" stands for atrial fibrillation or flutter in the following). The detector is preferably a component of a medical implant such as an implantable cardiac pacemaker or an implantable cardioverter/defibrillator.

2. Description of the Related Art

Atrial fibrillation is a state of disordered excitation of the atrial myocardium, possibly revolving around atrial flutter, in which the atrium provides practically no contribution to the pump output of a heart. In an intraatrial electrocardiogram, an atrial fibrillation may be recognized from a high excitation frequency and a low amplitude.

Treating an atrial fibrillation with the aid of implantable atrial defibrillators is known, for example. Examples of atrial defibrillators of this type and detectors for atrial fibrillation are found in U.S. Pat. Nos. 5,267,559, 5,433,729, 5,464,431, 5,464,432, 5,486,199, and 5,720,295.

Before the background of the known prior art, it is the object of the present invention to provide a detector for reliable recognition of AF, which may be implemented at an acceptable outlay and which has the highest possible sensitivity and also the highest possible specificity.

BRIEF SUMMARY OF THE INVENTION

According to the present invention, this object is achieved by a detector for AF which has an impedance measuring unit which has a measuring input, to which an atrial electrode line having an electrode for a unipolar measurement of an impedance in the atrium is to be connected or is connected. The impedance measuring unit is implemented to generate an atrial impedance signal, obtained in a unipolar manner, in such a way that the impedance signal for each atrial cycle, comprising an atrial contraction and the following relaxation of the atrium, comprises multiple impedance values detected at different instants within a particular atrial cycle. In other words: in operation, the impedance measuring unit samples the impedance at a frequency which is greater than the atrial contraction rate determined by the duration of the atrial cycle (AA interval).

The unipolar atrial impedance signal analyzed for this purpose is an impedance which is measured between a neutral electrode, such as the housing of an implantable defibrillator or cardiac pacemaker, and a small-area electrode near the wall in the atrium. Preferably, to determine this unipolar atrial impedance signal, a constant, pulsed measuring current is fed via the same two electrodes, such as an atrial tip electrode and the pacemaker or defibrillator housing, via which a voltage drop occurring as a result of the current pulses is also measured simultaneously.

In addition to the impedance measuring unit, the detector additionally has a signal input, via which a ventricle signal is to be supplied to the detector, which reflects the instants of ventricular contractions in chronological assignment to the atrial impedance signal. Such a ventricle signal may be an intraventricular electrocardiogram, but it may also be a signal derived therefrom such as the signal of a ventricular marker channel. In all cases, the ventricle signal is a signal which reproduces the instants of ventricular contractions, which are reflected as R waves in the intraventricular electrocardiogram. It is not decisive for the present invention whether the ventricle signal is a raw signal, as is obtained directly by detecting electrical potentials in the ventricle (i.e., an ECG) or a signal derived therefrom such as the signal of a marker channel.

Furthermore, in addition to the impedance measuring unit and the signal input for the ventricle signal, the detector has an analysis unit, which is implemented, to average multiple sequential impedance signal sections of a unipolar atrial impedance signal, which are each delimited by two sequential ventricular contractions, with one another, and to determine the maximum amplitude of the averaged unipolar atrial impedance signal section, to compare it to a comparison value, and if the maximum amplitude of the averaged unipolar atrial impedance signal is less than the comparison value, to generate an AF suspicion signal.

The AF suspicion signal identifies an atrial state in which the suspicion of an atrial fibrillation or atrial flutter exists.

The averaging of the atrial impedance curve over multiple ventricular cycles is not performed in such a way that the atrial impedance signal is compressed or stretched in the case of ventricular cycles of different lengths. Rather, either a starting or an end section of a particular atrial impedance section, which is longer than a shortest atrial impedance section to be averaged, is left out of consideration for the averaging.

The present invention is based on the recognition that in the case of AF, atrial contractions and ventricular contractions are disassociated in such a way that the synchronicity existing in healthy hearts does not exist between the atrial and ventricular contractions. This results in the atrial contractions occurring at different instants within a particular ventricular cycle in relation to sequential ventricular cycles. Therefore, if the atrial impedance signal is averaged cycle-by-cycle (in relation to the ventricular contractions) over multiple ventricular cycles, still existing peak amplitudes of the atrial impedance signal are averaged out so extensively that the averaged unipolar impedance signal no longer has peak amplitudes of noticeable size. This state is detected according to the present invention in that the averaged unipolar impedance signal is compared to a predefined, possibly automatically adjustable comparison value. If the peak amplitude of the averaged unipolar atrial impedance signal is less than the comparison value, AF exists with great probability. In this case, an AF suspicion signal is generated.

In a preferred embodiment variation, the analysis unit is implemented to always average the eight most current sections of the atrial impedance signal lying between two sequential ventricular contractions with one another. It has been shown that averaging over eight ventricular cycles already results in a sufficiently significant reduction of the peak amplitude of the atrial impedance signal. Furthermore, AF may already be established in this way after eight ventricular cycles. The averaging may also be performed over more than eight ventricular cycles, through which the specificity is elevated, but the detection speed is reduced simultaneously.

To produce the unipolar atrial impedance signal, the impedance measuring unit is preferably implemented to detect the atrial impedance at a sampling rate between 30 Hz and 300 Hz. A suitable current strength is in the range between 100 µA and 600 µA. The constant current output to determine the atrial impedance is preferably pulsed and has current pulses of identical duration in each case between 10 μsec and 20 μsec. The current pulses have a polarity alternating in pairs and are assembled into pulse packets in pairs. In order to be able to further exclude measurement artifacts, it is advantageous if the polarity sequence of sequential current pulse pairs alternates.

In order to elevate the specificity of the AF detector, the analysis unit preferably has a Wenckebach discriminator, which is implemented to respond to an AF suspicion signal and differentiate AF from an AV block II° Wenckebach type and cancel a previously produced AF suspicion signal again if necessary. The preferred embodiment variation is based on the recognition that in case of an AV block II° Wenckebach type, canceling of the peak amplitudes of the atrial impedance signal may occur even without the existence of AF if sections of the atrial impedance signal are averaged with one another over multiple ventricular cycles. This is related to the fact that the synchronicity between the atrial contractions and the ventricular contractions may also be lost in the case of an AV block II° Wenckebach type. The averaging of the atrial impedance signal results in ventricular contractions of asynchronous components of the atrial impedance signal being averaged out. In case of an AV block II° Wenckebach type, as a result of increasing fatigue up to exhaustion of the AV line (the natural stimulation transfer from the atrium to the ventricle, also referred to as atrioventricular transfer), the duration of a PQ interval —i.e., the interval between an atrial depolarization (and contraction) up to the beginning of the ventricular depolarization and contraction—increases periodically until it is so long that an atrioventricular transfer does not occur. Depending on whether the increase of the duration of the PQ interval remains constant or grows from heartbeat the heartbeat, the RR intervals (an RR interval indicates the duration of a ventricular cycle) will also remain constant or grow somewhat over multiple ventricular cycles until a transfer does not occur. Some ventricular cycles having approximately constant RR intervals and, adjoining thereto, a relatively long-lasting ventricular cycle having a relatively long RR interval or, if a cardiac pacemaker enters the two-chamber mode, a ventricular cycle having a relatively short cycle duration, i.e., a short RR interval, thus result periodically.

To differentiate an AV block II° Wenckebach type from AF, a Wenckebach discriminator is therefore preferably provided, which is implemented to perform this differentiation on the basis of a stability criterion. In a preferred embodiment variation, the Wenckebach discriminator continuously ascertains the average cycle duration (the average RR interval) RRm or even better the median value of the RR intervals over a number of N current ventricular cycles. If only one ventricular cycle always lies outside a predefined stability range in regard to the duration of its RR interval, this is an indication that it is not AF, but rather an AV block II° Wenckebach type. The predefined stability range is preferably defined by a differential dimension related to the mean value of the cycle duration in such a way that the mean value of the cycle duration RRm is multiplied by 1 plus/minus the differential dimension. The stability range thus results from $RRm*(1+/-d)$, d being the differential dimension.

If at least two RR intervals also lie outside the stability range thus defined from time to time, the Wenckebach discriminator excludes the existence of an AV block II° Wenckebach type and confirms the AF suspicion signal, i.e., the AF detector then finally detects AF.

In a preferred embodiment variation, the Wenckebach discriminator is implemented to operate in the following way:

For the case that the peak amplitude of the averaged atrial impedance signal has fallen below the predefined comparison value, i.e., for the case in which the analysis unit has generated an AF suspicion signal, the Wenckebach discriminator is applied, which produces a counter value in the following way. For this purpose, the Wenckebach discriminator may alternately be continuously active in the background, or may analyze a stored RR interval trend only upon the existence of an AF suspicion signal. Firstly, the Wenckebach discriminator calculates the stability range as the RR stability interval for each current ventricular cycle by multiplying the duration of the RR intervals RRm (mean cycle duration of the ventricular cycles) averaged over the current N ventricular cycles by two differential factors and thus determines the upper and lower boundary of the particular current RR stability interval (the current stability range). The differential factor results from the sum of 1 plus a predefined differential dimension d, which is 0.25, for example, or 1 minus d, respectively. The ventricular cycle duration averaged over N ventricular cycles may be the mean value of the current N RR intervals or preferably the median of a number N of current RR intervals. Alternatively, the mean ventricular cycle duration may also be produced by a recursive filter using N as a type of "time constant". A suitable value for the number N is between 5 and 8.

The Wenckebach discriminator checks for each ventricular cycle whether the corresponding RR interval lies within the RR stability interval $RRm * (1+/-d)$ produced in the way above. If a particular current RR interval lies outside this current valid RR stability interval and if the following RR interval again lies within the RR stability interval, the count of the counter of the Wenckebach discriminator is incremented up by 1. The count of the counter of the Wenckebach discriminator may reach a predefined maximum value Nmax of 20, for example, at most, i.e., as soon as the count 20 has been reached, this count may no longer be incremented up. As soon as two sequential ventricular cycles have RR intervals which lie outside the RR stability interval or a multiple of, for example, 20 sequential RR intervals lie inside the RR stability interval, the counter of the Wenckebach discriminator is incremented down by 1 again. If the count of the counter of the Wenckebach discriminator reaches a predefined count threshold Nth of 10, for example, the Wenckebach discriminator detects the presence of an AV block II° Wenckebach type and cancels the AF suspicion signal. This avoids an atrial defibrillation being triggered, even though there is no atrial fibrillation, but rather an AV block II° Wenckebach type.

Instead of analyzing the stability of the RR intervals in the way described above, the Wenckebach discriminator may also be implemented to analyze the stability of the rate of the ventricular contractions.

BRIEF DESCRIPTION OF THE DRAWINGS

The present invention will now be explained in greater detail on the basis of an exemplary embodiment with reference to the attached figures. In the figures.

DETAILED DESCRIPTION

Figure 1:
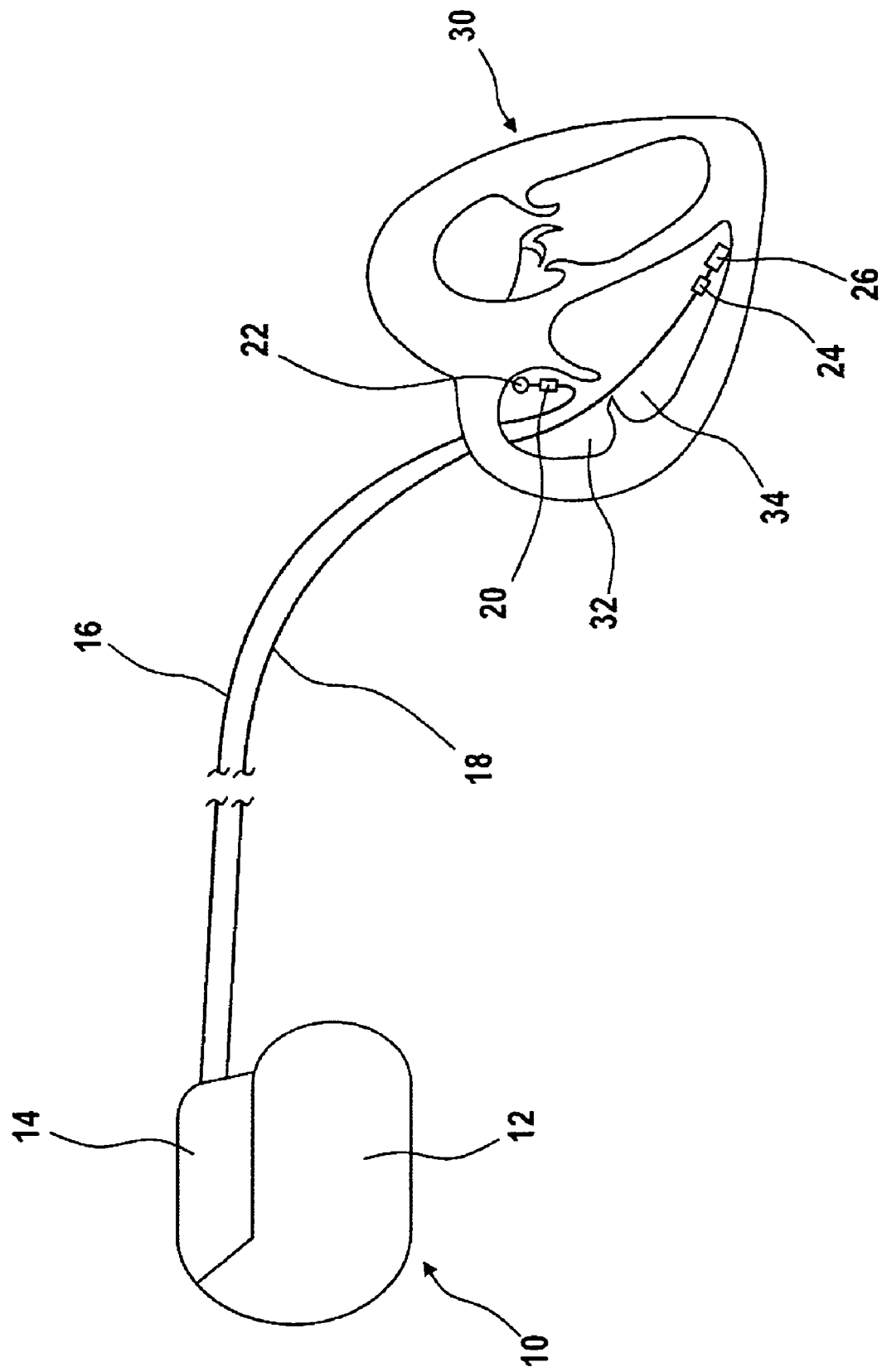
FIG. 1 shows a two-chamber cardiac pacemaker having ventricular and atrial electrode lines connected thereto and placed in the heart.

FIG. 1 shows an implantable cardiac pacemaker 10, which has a hollow housing 12 made of metal and a header 14 made of transparent, insulating plastic, in which terminals for electrode lines are situated. An atrial electrode line 16 and a ventricular electrode line 18 are connected to the cardiac pacemaker 10.

The atrial electrode line 16 carries an atrial ring electrode 20 and an atrial tip electrode 22 in the area of its distal end.

The ventricular electrode line 18 carries a ventricular ring electrode 24 and a ventricular tip electrode 26 on its distal end.

As may be seen from FIG. 1, the distal ends of the atrial electrode line 16 and the ventricular electrode line 18 are placed in a heart 30 in operation of the cardiac pacemaker 10, in such a way that the atrial ring electrode 20 and atrial tip electrode 22 are located in the right atrium 32 of the heart 30, while the ventricular ring electrode 24 and the ventricular tip electrode 26 are situated in the apex of a right ventricle 34 of the heart 30. It is advantageous for the present invention if at least the atrial tip electrode 22 is wall-mounted, i.e., presses directly against the cardiac muscle tissue (myocardium) in the atrium 32.

Figure 2:
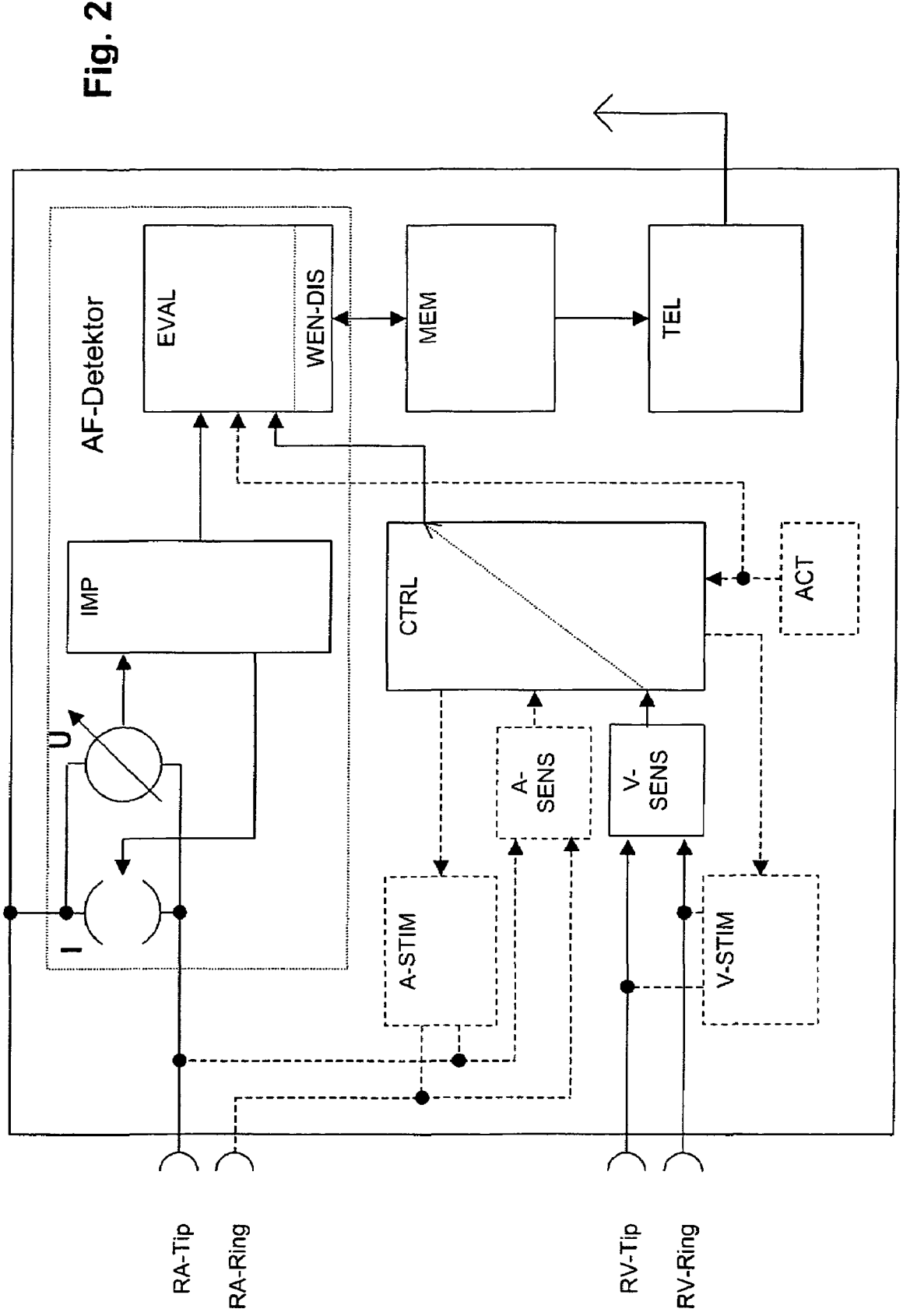
FIG. 2 shows a schematic block diagram of the cardiac pacemaker from FIG. 1 having an AF detector according to the present invention.

The essential electrical components of the cardiac pacemaker are situated in the interior of the hollow housing 12 of the cardiac pacemaker 10 and electrically connected via the header 14 to terminals for the electrodes of the atrial electrode line 16 and the ventricular electrode line 18. An electrical terminal RA ring for the right-atrial ring electrode 20, a further electrical terminal RA tip for the right-atrial ring electrode 22, an electrical terminal RV ring for the right-ventricular ring electrode 24, and an electrical terminal RV tip for the right-ventricular tip electrode 26 are shown in FIG. 2.

In a manner typical for a two-chamber cardiac pacemaker, the terminals RA ring and RA tip are connected to an atrial stimulation unit A-STIM and an atrial sensing unit A-SENS and the terminals RV ring and RV tip are connected to a ventricular simulation unit V-STIM and a ventricular sensing unit V-SENS. The stimulation and sensing units are each connected to a central control unit CTRL and allow, together therewith, demand-dependent stimulation in a demand mode, such as DDD.

An AF detector for detecting atrial fibrillation or flutter (AF) is of essential importance for the present invention. The AF detector comprises multiple components which are framed in FIG. 2 by a dashed line. These components include an impedance determination unit IMP, which is connected to a constant current source I and a voltage measuring unit U. The impedance determination unit IMP forms an impedance measuring unit together with the constant current source I and the voltage measuring unit U.

A further component of the AF detector is an analysis unit EVAL, which in turn has a Wenckebach discriminator WEN-DIS as a component. A counter as a component of the Wenckebach discriminator WEN-DIS is not shown in greater detail.

The constant current source I of the impedance measuring unit is connected to the terminal RA tip for the right-atrial tip electrode 22 and, in addition, to the metallic hollow housing 12 of the cardiac pacemaker 10 as the neutral electrode. This is also true for the voltage measuring unit U, which is implemented to measure the voltage drop which is applied via these two electrodes when the constant current source I outputs a measuring current to measure the intraatrial impedance.

Figure 3:
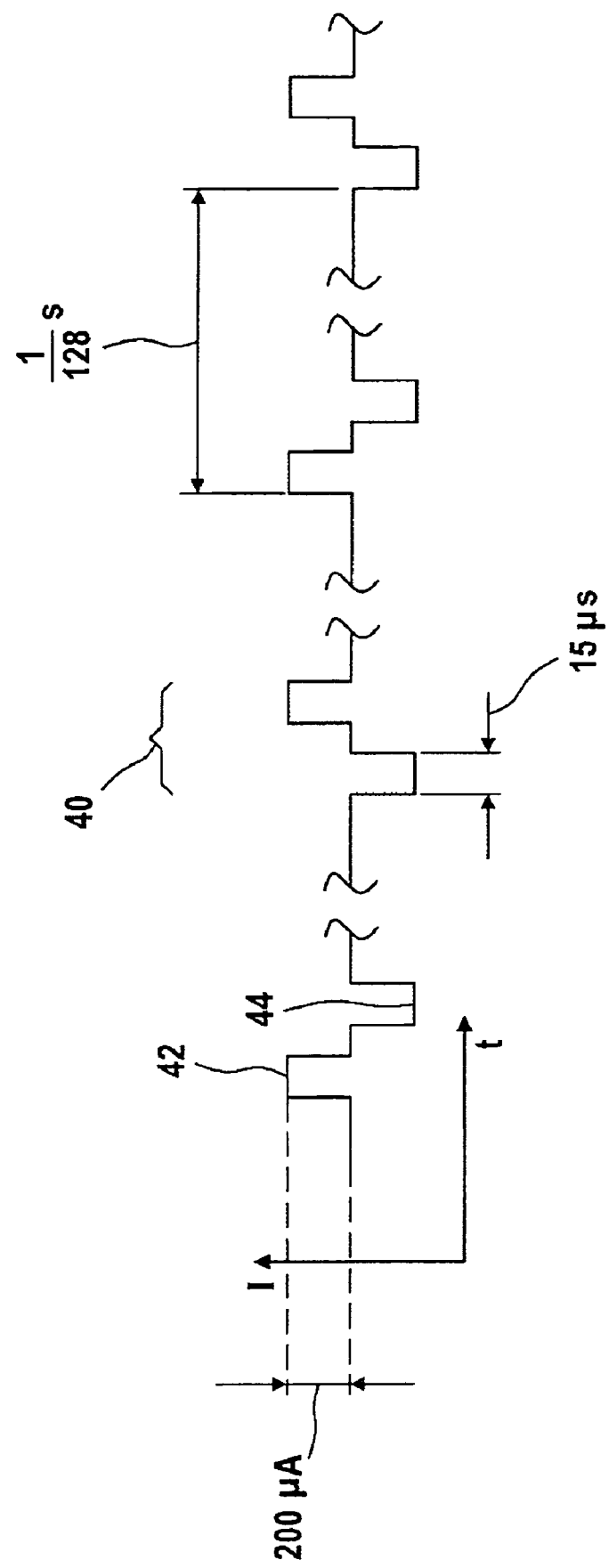
FIG. 3 shows an illustration of the preferred measuring current used for ascertaining the unipolar intraatrial impedance.

The constant current source I is implemented to generate and deliver a measuring current in the way outlined in FIG. 3. 128 times per second, the constant current source I generates a current pulse pair 40 of a total of 45 μsec duration, which is formed by two current pulses 42 and 44, each lasting 15 μsec, of identical absolute current strength but opposite polarity. A pause, also of 15 μsec duration, is provided between the two current pulses 42 and 44 in each case. The current pulse pairs 40 repeat every 128 th of a second. The polarity sequence alternates from current pulse pair to current pulse pair, as shown in FIG. 3, i.e., a first current pulse pair begins with a positive current pulse 42 and ends with a negative current pulse 44, while the following current pulse pair 40 begins with a negative current pulse and ends with a positive current pulse. The production of artifacts is avoided in this way.

As may be seen from the above description, the atrial impedance is sampled at a sampling rate of 128 Hz. The impedance determination unit IMP calculates an impedance value from the values for the current strength and the associated measuring voltage through quotient calculation and generates a unipolar atrial impedance signal in this way, which is supplied from the impedance determination unit IMP to the analysis unit EVAL. The atrial impedance signal is analyzed in the way described above in the analysis unit EVAL. In order to be able to perform this analysis, a ventricle signal is additionally supplied to the analysis unit EVAL. This ventricle signal represents the instants of ventricular contractions in chronological assignment to the atrial impedance signal.

The ventricle signal is produced in a known way per se with the aid of the control unit CTRL of the cardiac pacemaker, which is connected to the ventricular sensing stage V-SENS. In operation, the ventricular sensing stage is connected in turn to the ventricular ring electrode 24 and the ventricular tip electrode 26 via corresponding terminals RV ring and RV tip of the cardiac pacemaker 10.

As already described at the beginning, the analysis unit EVAL produces signal sections of the atrial impedance signal lying between each two sequential ventricular contractions and averages the signal sections over eight current ventricular cycles in each case In healthy hearts, a particular ventricular contraction occurs a relatively constant atrioventricular transfer time after an atrial contraction, so that a synchronicity exists between atrial and ventricular contractions. The atrial impedance signal averaged in the way described above reproduces the typical curve of the atrial impedance between two sequential ventricular contractions in this case and has an amplitude maximum at an instant at which the atrial contraction occurs. This instant is before a particular, following ventricular contraction and has a chronological spacing thereto, which approximately corresponds to the atrioventricular transfer time.

In case of AF, but also in case of an AV block II° Wenckebach type, the synchronicity between atrial contractions and ventricular contractions does not exist. This results in the typical maximum amplitudes of the curve of the atrial impedance averaging out between two ventricular contractions when averaged over multiple ventricular cycles, since they occur at different instants in relation to a particular ventricular cycle.

The present invention makes use of this state of affairs in that the analysis unit EVAL detects a nonexistent atrioventricular synchronicity by analyzing the averaged atrial impedance signal. For this purpose, the peak amplitude of the averaged atrial impedance signal is compared to a comparison value and a nonexistent atrioventricular synchronicity is detected when the peak amplitude of the atrial impedance signal is less than the comparison value. Since a nonexistent atrioventricular synchronicity may also have its origin in an AV block II° Wenckebach type, the analysis unit EVAL, in the preferred embodiment variation shown here, additionally has a Wenckebach discriminator WEN-DIS, which is implemented to detect the existence of an AV block II° Wenckebach type in the way described at the beginning, if the analysis unit EVAL has first established a lack of atrioventricular synchronicity and subsequently generated an AV suspicion signal. The Wenckebach discriminator WEN-DIS acts as a type of filter in the output of the analysis unit EVAL and ensures that the analysis unit EVAL only outputs an AF suspicion signal if the analysis unit has established the lack of atrioventricular synchronicity and, in addition, the Wenckebach discriminator has established the nonexistence of an AV block II° Wenckebach type.

Figure 4:
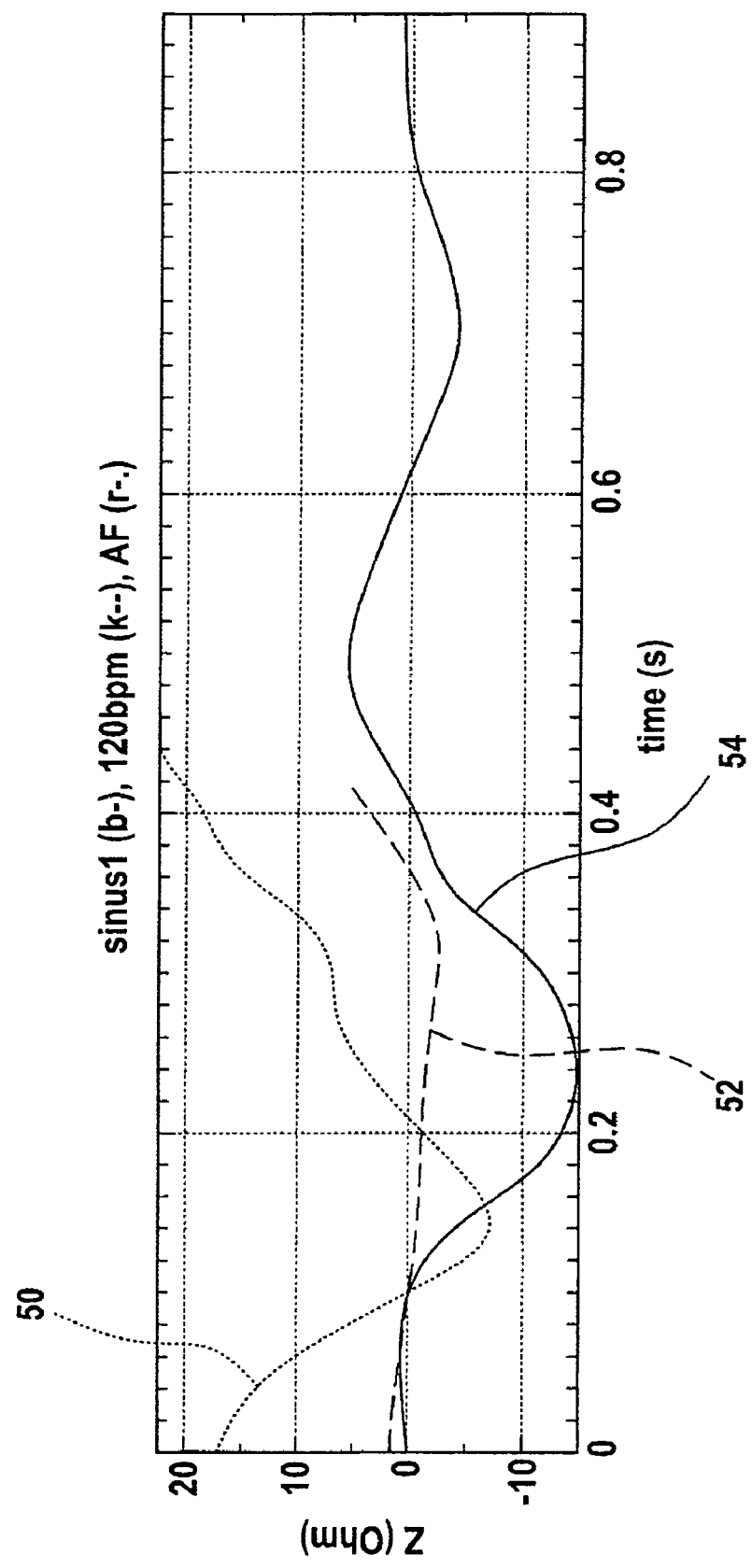
FIG. 4 shows examples of the curve of the peak amplitude of averaged atrial impedance signals for different heart states.

Three different intraatrial impedance curves are shown in FIG. 4 to explain the mode of operation of the analysis unit EVAL, namely for the case of the healthy heart (curve 50), for the case of the stimulated heart (curve 52), and for the case of the presence of AF (curve 54). It may be recognized clearly that the maximum amplitude of the averaged intraatrial impedance signal is comparatively very small in the case of an AF.

For long-term diagnostic purposes, the phases of the presence of an AF suspicion signal are stored in a memory MEM and may be transmitted wirelessly to a service center, for example, using a telemetry unit TEL.

In addition, the cardiac pacemaker has the typical components for rate-adaptive stimulation of the ventricle and the atrium, such as the stimulation units V-STIM and A-STIM, the sensing units V-SENS and A-SENS, the control unit CTRL and an activity sensor ACT, which allows the particular stimulation rate to be adapted to the physiological demand of a patient.

Moreover, the cardiac pacemaker may also be implemented as a cardioverter/defibrillator, particularly as an atrial defibrillator, and have atrial stimulation units adapted for this purpose, as are known in principle from the prior art.

What is claimed is:

1. A detector for atrial fibrillation or flutter (AF) comprising:
an impedance measuring unit comprising a measuring input, to which an atrial electrode line having an electrode for a unipolar measurement of an impedance in an atrium is connected and is implemented to generate an atrial impedance signal, obtained in a unipolar manner, in such a way that an impedance signal for each atrial cycle, comprising an atrial contraction and a following relaxation of said atrium, comprises multiple impedance values detected by said impedance measuring unit at different instants within a particular atrial cycle;
said impedance measuring unit comprising a signal input, via which a ventricle signal is to be supplied to said detector, which reflects instants of ventricular contractions in chronological assignment to said impedance signal;
an analysis unit configured to average multiple sequential impedance signal sections of a unipolar atrial impedance signal, in which each impedance signal section is delimited by two sequential ventricular contractions, with one another, and to determine a maximum amplitude of an averaged unipolar atrial impedance signal section; and
said analysis unit configured to compare said maximum amplitude to a comparison value, and if said maximum amplitude of said averaged unipolar atrial impedance signal is less than said comparison value, generate an AF suspicion signal.

2. The detector according to claim 1, wherein said analysis unit is implemented to average a particular eight most current impedance signal sections with one another.

3. The detector according to claim 1 wherein said impedance measuring unit is implemented to detect a unipolar intracardial impedance at a sampling rate between 30 Hz and 300 Hz.

4. The detector according to claim 1 wherein said impedance measuring unit is configured to measure a unipolar intracardial impedance, to generate current pulses having a current strength between 100 µA and 600 µA and deliver said current pulses via a neutral electrode and an atrial electrode and to measure a voltage drop occurring during a delivery of said current pulses via these two electrodes.

5. The detector according to claim 4 wherein said impedance measuring unit is implemented to deliver current pulses having an identical duration in each case, which is between 10 µsec and 20 µsec.

6. The detector according to claim 5 wherein said impedance measuring unit is implemented to deliver two current pulses, of identical duration and identical absolute current strength, but different polarity, in pairs in each case.

7. The detector according to claim 6 wherein said impedance measuring unit is implemented in such a way that a polarity sequence of sequential current pulse pairs alternates.

8. The detector according to claim 1 wherein said analysis unit has a Wenckebach discriminator, which is implemented to respond to an AF suspicion signal and differentiate AF from an AV block II° Wenckebach type and cancel said AF suspicion signal.

9. The detector according to claim 8 wherein said Wenckebach discriminator is implemented to calculate a mean value of a cycle duration of a ventricular cycle, RR interval, over a predefined number of ventricular cycles based on said ventricle signal, and, if said AF suspicion signal exists, to compare a duration of a current ventricular cycle to said mean value of said cycle duration and check whether only a single ventricular cycle or multiple sequential ventricular cycles deviate in regard to their duration by more than a predefined differential dimension from said mean value of said cycle duration and, in a first case, to cancel said AF suspicion signal again.

10. The detector according to claim 9 wherein said Wenckebach discriminator is implemented to calculate a differential dimension from said mean value of said cycle duration of ventricular cycles calculated over a predefined number of current ventricular cycles by multiplying said mean value with a predefined constant factor.

11. The detector according to claim 9 wherein said Wenckebach discriminator is implemented to generate a Wenckebach signal for every ventricular cycle in which a single ventricular cycle deviates in regard to its duration by more than a predefined differential dimension from said mean value of said cycle duration.

12. The detector according to claim 11 wherein said Wenckebach discriminator has a counter which is implemented to increase its count by 1 if said Wenckebach discriminator has generated a Wenckebach signal for an isolated current ventricular cycle.

13. The detector according to claim 12 wherein said counter is implemented to reduce its count by 1 if said Wenckebach discriminator has detected that two current sequential ventricular cycles deviate by more than the predefined differential dimension from said mean value of said cycle duration or no Wenckebach signal has been generated for multiple, at least five sequential current ventricular cycles.

14. The detector according to claim 13 wherein said analysis unit is implemented to cancel said AF suspicion signal and reset said counter if said count exceeds a predefined count threshold.

* * * * *